United States Patent [19]

Fischer

[11] Patent Number: 4,691,559
[45] Date of Patent: Sep. 8, 1987

[54] DEVICE FOR MEASURING THE PROPERTIES OF SOLID MATERIALS WHICH CAN BE DERIVED FROM THE BEHAVIOR OF A PENETRATING BODY

[76] Inventor: Helmut Fischer, Industriestrasse 21, 7032 Sindelfingen-Maichingen, Bundesrepublik, Fed. Rep. of Germany

[21] Appl. No.: 699,430

[22] Filed: Feb. 7, 1985

[51] Int. Cl.[4] .............................................. G01N 3/48
[52] U.S. Cl. ....................................................... 73/81
[58] Field of Search ...................... 73/81, 818, 1 J, 1 R

[56] References Cited

U.S. PATENT DOCUMENTS

| 4,094,188 | 6/1978 | Bellouin et al. | 73/81 |
| 4,104,901 | 8/1978 | Sidaway | 73/81 |
| 4,118,975 | 10/1978 | Iwasaki | 73/81 |
| 4,331,026 | 5/1982 | Howard et al. | 73/1 R |
| 4,450,713 | 5/1984 | Arimatsu | 73/81 |

FOREIGN PATENT DOCUMENTS

| 956174 | 3/1957 | Fed. Rep. of Germany | 73/1 J |
| 24883 | 3/1978 | Japan | 73/81 |
| 48302 | 2/1983 | Japan | 73/81 |
| 665245 | 5/1979 | U.S.S.R. | 73/81 |
| 48311 | 11/1983 | U.S.S.R. | 73/81 |

Primary Examiner—Stewart J. Levy
Assistant Examiner—Robert R. Raevis

[57] ABSTRACT

A guidance arm guides a penetrating body into solid materials. An electromotive drive connected to the guidance arm urges the penetrating body with a specific, but variable force onto the surface of the material. A suspended distance-measuring device has a probe rigidly connected to a backlash-free follower and a metallic substrate with an inert coating connected to the guidance arm. The follower is finely adjusted in the direction of motion of the penetrating body, and is switched off when the penetrating body has been set down onto the material and the distance-measuring device measures a prespecified distance. A voltage output representing the depth of penetration is fed from the distance-measuring device to an electrical evaluation circuit.

45 Claims, 16 Drawing Figures

DEVICE FOR MEASURING THE PROPERTIES OF SOLID MATERIALS WHICH CAN BE DERIVED FROM THE BEHAVIOR OF A PENETRATING BODY

The present invention relates to an apparatus for non-destructive, absolute measurement of the properties of solid materials which is derived from the behavior of a body penetrating such materials, having a penetrating body, a guidance device for guiding the penetrating body into the materials, and an electrical evaluation circuit.

BACKGROUND OF THE INVENTION

Probably the best known example of the use of the behavior of a penetrating body in a material to determine its properties is the measurement of material hardness. Here there exist a considerable number of methods, for example, Shore hardness measurement, Vickers hardness measurement, Rockwell hardness measurement, Brinell hardness measurement, Herberts pendulum etc.. In view of the fact that the surface layer is fully or partially destroyed, however, these methods cannot be used in a great many areas of application. For example, if the hardness of paint is to be measured, it may be the case that the paint layer is not completely penetrated. Despite this, the paint is damaged and it is possible that a rust spot at the test point could form the nucleus of corrosion, whereas the rest of the paint layer is still in order. For this reason, the finished object is not measured, rather a test specimen. The test specimen, however, is not the finished object.

There are also non-destructive methods for measuring the properties of solid materials which can be derived from their behavior under penetration. For example, it is known that, by placing an ultrasonic probe on a material, the frequency mismatch can be measured. This method is very sensitive to the degree of coupling with the test object. In addition, it is not the hardness alone which is measured, because the measured value depends substantially on the modulus of elasticity of the material, the thickness of the coating and the shape of the object, in particular, on the thickness. The method can only be used for comparative assessments and not for absolute measurements.

A further non-destructive method giving absolute measurements was described in the "Industrie-Anzeiger" of 2nd Dec., 1981 under the (translated) title "Method for testing the case hardness distribution of forgings". The device described is very expensive. It is also so large that the object must be brought to the device; the reverse is not possible. A force is applied inductively and the depth of penetration is measured by optical displacement measurement. Due to the sensor system employed for measurement, it is not possible to safely determine the depth of penetration in the micrometer range. The method is designed for measurement of case hardness with typical penetration depths of 500 um. Similar to the case of a micrometer screw gauge, the system requires a very rigid yoke. The depth of penetration at a given force is converted by a difficult-to-use nomogram, since the measured value is a complicated function of the force applied.

An apparatus has been described in the German Patent Application P No. 34 08 554.8 corresponding to U.S. patent application Ser. No. 606 922, the Japanese Patent Application No. 75655/84 and the English Patent Application No. 840 9155 which is inexpensive to manufacture, which is so small that it can be brought to the place of use, which measures non-destructively, which allows reproduceable, absolute measurements, which can also actually measure the hardness of the topmost coating in the case of inhomogeneous materials, which leads to simple functional relationships, which has no exotic system such as ultrasonic sensors, interference measurements or similar whatsoever and can also be used by unskilled personnel.

The invention specified there has the following advantages:

(A) The probes, which are already known, allow very precise measurement of coating thickness over a wide range of thicknesses. In view of the fact that very precise absolute measurements are possible, it is also possible to measure coating thickness differences to high precision. For example, for a coating thickness of $20\mu m$, a change in coating thickness of $0.05\mu m$ is easily detected. Alternatively, in the range from 100 to $500\mu m$ a change of coating thickness of $0.1\mu m$ is measured with ease. Such small changes in coating thickness can be generated by extremely low contact forces. To give an idea of the size of the necessary forces, these lie, for example, in the range of 0.05 to 1N.

(B) These minimal forces do not destroy even the softest coating.

(C) In view of the fact that the necessary forces are very low, there is no danger that the device will bend under its own weight and it is possible to make it rigid enough for the purpose here described with very little expenditure of material.

(D) With such low forces, measurements are actually only made in the surface zone which, in any case, provides the most important testimony in most applications.

(E) With such small measurement areas the measurements themselves leave no traces whatsoever.

(F) In view of the fact that high energies need not be applied high energies need not be supplied either. It is, therefore, perfectly plausible to use the device with battery power.

(G) The measurement is practically displacement-free, with all the resulting consequences.

(H) The device can be used to measure on very small and/or curved surfaces.

Probes which measure such thick coatings with high precision have been known for many years, and are described, for instance, in German Utility Patent No. 72 43 915, German Utility Patent No. 73 36 864, German Patent Disclosure No. 25 56 340 or the still to be published German Patent Application P No. 33 31 407.

Figures 2, 2A:
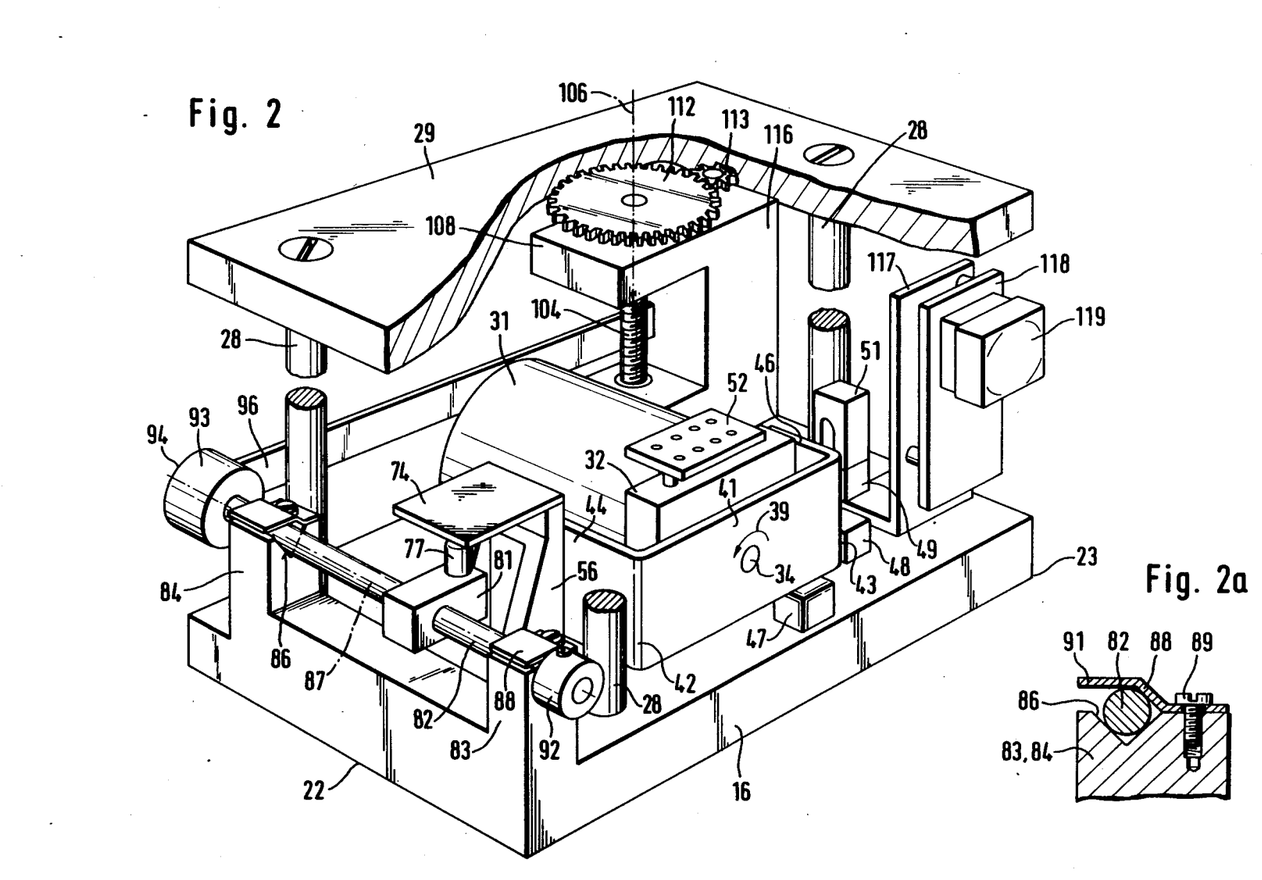
FIG. 2 A prospective, partially sectioned view of the device.
FIG. 2a. A cross-section through a backlash-free bearing.

The invention described in German Patent Application P No. 34 08 554.8 has, however, the following disadvantages:

(A) The coating to be measured must be deposited on a substrate, such as, for example, in FIG. 2 the coating 22 is deposited on the substrate 23. If probes which are based on the magnetic method are used, then, the coating must be deposited on soft iron. If probes which are based on the eddy-current method are used, the coating must be deposited on, for example, aluminium or a similar metal. It is, however, desirable that materials which are not deposited on a substrate can be measured. It is true that, for instance, paints are very frequently applied to magnetic or non-magnetic substrates. In many other cases, however, this is not so.

(B) The probes must be specially manufactured because their tips are at the same time the penetrating body.

(C) Depending on whether the coating is deposited on a magnetically soft material or a non-magnetic material either one type of probe or another type of probe must be used. The expert who is, for instance, only interested in measuring the hardness or the flow behaviour of such materials often does not know what substrate lies underneath the coating to be measured and very frequently has absolutely no or only a very hazy knowledge of the magnetic properties of the substrate.

OBJECTS AND STATEMENT OF THE INVENTION

The objects of this invention are to provide a device of the type specified in the introduction which exhibits all the advantages of the previous invention, and which allows the properties of materials as indicated above to be measured without having first to be sure whether or not the coating to be measured is deposited on a substrate.

The objects are achieved, according to the invention, by means of (a) an electromotive drive connected to the guidance device, which urges the penetrating body with a specific, but variable force onto the surface of the material, (b) a suspended distance-measuring device having a first and a second section, which allows distance measurement in the direction of motion of the penetrating body, (c) the first section being rigidly connected to the penetrating body, (d) a backlash-free follower connected to the second section, (e) means for finely adjusting the follower in the direction of motion of the penetrating body, the means switching off when the penetrating body has been set down onto the material and the distance-measuring device measures a prespecified distance, and (f) means for feeding a voltage output representing the depth of penetration from the distance-measuring device to the electrical evaluation circuit.

As in the previous invention, a guidance device is provided in the form of an electromotive drive. In this case, however, the penetrating body itself can be used in conjunction with the drive and the probe does not have to carry a penetrating body at its tip. Now, however, the thickness of the coating to be measured with respect to the substrate is not quite directly measured as was previously the case but rather the penetration of the penetrating body at various forces is measured at another position in the device. This displacement required by the penetrating body in order to lower itself onto the material is no longer measured by the suspended distance measuring device, but rather the starting point of the measurement is shifted to that position which represents the surface of the material. For the measurement, the distance measuring device starts with a predetermined distance which, of course, must be greater than the expected penetration depth.

Advantageously, the invention includes the following additional features.

The guidance device is a lever rigidly fixed to the drive shaft of the electromotive drive, which carries the penetrating body tangential to its rotary motion. This feature avoids an intermediate gear with its play and, since the measurement is practically displacement-free, the rotary motion of the electromotive drive leads to a quasi linear motion of the penetrating body.

The penetrating body is a diamond. The feature provides a penetrating body which is of the hardest known material, which is magnetically indifferent, and, the flanks of which can be polished to a very high degree, so that, when the varying force is applied, it does not or only very slightly scratch the walls of the indentation. The penetrating body can, thus, be made as a true wedge which, because of the varying force, has quite another significance than that of the well-known hardness measurement methods which also use a diamond.

The diamond is a pyramid-shaped Vickers diamond. The feature allows some of the wealth of experience associated with Vickers hardness measurements to be used.

The diamond is a conical Rockwell diamond. The feature allows some of the wealth of experience associated with Rockwell hardness measurement to be used.

The penetrating body is a Brinell steel ball. The feature allows some of the wealth of experience associated with Brinell hardness measurements to be used.

The penetrating body is exchangeable and screwed into the guidance device. The feature allows either worn penetrating bodies to be exchanged or new ones or different penetrating body shapes to be used.

Means exert a permanent force gently on the guidance device for biassing the guidance device against the direction of motion of the penetrating body. The feature ensures that the penetrating body is safely in its starting position for the measurement, i.e. in raised position, at the start of the measurement.

The permanent force means comprises at least one magnet. The feature avoids the disadvantages of a spring, such as fatigue, hysteresis, friction, etc.. As a magnetic device which requires no additional energy, the permanent magnet is preferred. In particular, two permanent magnets are preferred which, depending on their position with respect to the guidance device lever described above, are to be found to the right or left of the drive shaft.

Two magnets are aligned in the direction of the motion of the penetrating body. The feature ensures that these magnets produce no lateral forces.

A stop is provided for the guidance device which limits the movement of the guidance device with respect to the direction of motion of the penetrating body. The feature prevents the magnets from touching each other, since, in the case of permanent magnets, very large initial forces at the electromotive drive would be necessary. The stop allows the magnets to be kept at a distance and allows nearly constant forces over that range which comes into question at all for the pivoted motion.

The distance-measuring device comprises a probe for measuring thin coatings fixed to one of the two sections and a counter-pole body fixed to the other section. The feature allows probes or special constructions which are well known and well proven in distance measurements to be used. The measurement of the penetration depth of the penetrating body is derived from a distance measurement, and the distance measurement is performed under constant conditions since they are made in the device. Thus, the shape of the indentation made by the penetrating body is not observed rather a distance measurement of the penetration depth is made directly. Normally, the distance measuring device would be found in the inside of the device. The probe is, thus, at a distance from a material to be measured. The probe can thus be used even when the material to be measured is very warm, which, for example, is very important in the case of paints. By the time the heat penetrates to the probe, the measurement is long completed because the three to six points in a measurement cycle require only a few seconds in the case of hardness measurement. If the fall-off in hardness as a function of temperature is to be measured, which is particularly important in the case of plastics, then, this can be done by cooling the inside of the device. The diamond or another penetrating body is impervious to heat. Since the distance measuring device can be positioned inside the device the inside of the device can be cooled.

The distance-measuring device has a resolution that lies in the range of at least one hunredth of a micrometer. The feature means that the measurement error even for very hard materials is slight. If the penetrating body, for example, penetrates to a depth of 1 μm and the resolution has the specified degree, then, the error due to the resolution is of the order of only a few percent.

The probe works on the magnetic field principle. The feature allows commercial, fully developed, highly precise probes to be used. If capacitive distance measuring devices are accessible, a capacitive probe allows these to be used.

The probe works on the field-plate principle. The feature allows iron to be used as the counter-pole body for the distance measuring device.

The distance-measuring device works with an optical graduated rule, a light pointer and a mirror. The distance measurements is accordance with this feature are contact-free and of high resolution. The same is true of probes that work on the magnetic field, capacitive and field plate principles.

The counter-pole body comprises a metallic substrate having an inert thin coating. The feature ensures that the surface of the counter-pole body does not change with time, i.e. does not oxidize. This would mean that in the course of time its surface geometry would change.

The inert thin coating is a gold coating. The feature prevents oxidation by the simple means of providing a coating which does not crack, which, for example, might be the case if the covering coating was of vapour-deposited silicon.

The counter-pole body is arranged perpendicular to the probe. The feature reduces the danger of foreign bodies, for example, dust settling on the counter-pole body.

The counter-pole body is quasi infinitely large with respect to the probe field. The feature means that no correction factors are required if a calibration value of the distance measurement should assume the distance value infinity.

The probe is secured on the backlash-free follower and the counter-pole body is secured on the guidance device. The feature ensures that the leads for the probe have absolutely no effect on the guidance device, leaving only friction as a possible undesirable force. The purpose of the follower is simply to follow and not to determine any forces.

The distance-measuring device is aligned with the penetrating body, as seen from the direction of motion of the penetrating body. The feature ensures that no undesirable forces act on the electromotive drive and its bearings when the sections of the distance measuring devide are set down upon each other.

The backlash-free follower comprises a threaded spindle. The feature ensures that the possibility exists of making the precision of following sufficiently fine.

The threaded spindle stands parallel to the direction of motion of the penetrating body. The feature avoids the use of further joints with their associated play.

An electric motor drives the threaded spindle, and means effect substantial gear reduction between the electric motor and the threaded spindle. The feature allows the threaded spindle to be driven simply and in addition finely in both directions of rotation.

A pivoting shaft is provided close to the distance-measuring device and perpendicular to the direction of motion of the penetrating body, and one of the two sections of the distance-measuring device is fastened to the pivoting shaft. The feature allows the necessary possibilities of movement for the distance measuring device to be realized mechanically very directly and simply, backlash-free and with a minimum of joints.

A single, two-ended lever is fastened at one end to the pivoting shaft, and guided at its other end by the threaded spindle. The feature ensures that the device remains small but, despite this, has fine movement possibilities for the follower.

The lever is a broad leaf spring, the rigid direction of which lies parallel to its direction of movement, having a cup at its other end which engages backlash-free on the flanks of the thread of the threaded spindle, and is pressed into the thread in the bending direction for pretensioning the leaf spring. The feature allows on one hand an extremely stiff and on the other hand a very light lever which, in addition, ensures freedom from play.

The pretensioning is so light that, when the leaf spring arrives at its end position, the cup disengages the thread. The feature ensures that the threaded spindle need not be exactly stopped, but despite this, nothing is destroyed.

The pivoting shaft and the drive shaft are arranged parallel to each other and at the same level. The feature means that, on one hand, the device is flat and, on the other hand, the movements of the distance measuring device and the penetrating body can be compared more easily.

The electric motor that drives the threaded spindle is at the other side of the electromotive drive, as seen from the probe, and the electric motor is fastened to the device base at one end. The feature allows on one hand the lever to have optimum length, and, on the other hand, the magnetic field of the electric motor does not interfere with the probe in as far as it has magnetic coils.

The threaded spindle has bearings at both ends, and at least one of the bearings is a collar-bearing. The feature allows an extraordinary degree of freedom from backlash. It then no longer matters whether the electric motor and/or its electromotive drive have a lot or a little backlash.

The device base stands on three feet, two of which lie on a common line with the tip of the penetrating body. The features allow measurements to be easily made on the circumference of curved bodies such as, for example, pipes or other prismatic objects.

The common line runs parallel to one of the lateral edges of the device. The feature allows a clearer idea of where measurements should be made for prismatic objects.

The two feet lying on the common line are hardened and shaped as spherical cups. The features ensure that the device stands optimally independent of the shape of the material to be measured.

A start switch is provided. The feature ensures that the device is not handled once it has been started. Since, in any case, the device requires a few tenths of a second to prepare the electronics, any vibrations caused by the placing of the device on the material have, by this time, long since subsided.

The apparatus is calibrated by the following method:
(a) switching on the apparatus,
(b) bringing the distance-measuring device to a first position that corresponds to a distance value,
(c) storing that value in a memory device, and
(d) entering a nominal distance as a second value into said memory device.

Thus, the first distance value is repeatedly determined so that any changes in the devices have no effect. The second distance value need not be specially determined but is rather already stored in the device.

The first value corresponds to a quasi infinite value. The feature ensures that the first value can be determined very easily.

The second distance value corresponds to a value which is very much larger than that of the anticipated penetration depth. The feature ensures that the numerical value of this value is always available for forming the difference in order to determine the penetration depth.

The nominal distance value lies in the deca micrometer range, preferably between 10 and 80 μm, in particular 40 μm±30%. The values specified are well proven in practice for the measurement and are easily electrically or mechanically managed without great expenditure of effort.

The circuit for evaluating signals received from the apparatus comprises an A/D converter connected to the distance measuring device, a distance nominal-actual comparator driven by the A/D converter at its actual input, a motor final control element driven by the nominal-actual output of the comparator, a follower servo-motor driven by the motor final control element via a "motor on/off line" and a "motor nominal value-/infinity line", a microprocessor connected to the motor control, a programmable current regulator having a current nominal-actual comparator, the electromotive drive being controlled by the current nominal-actual comparator via a current final control element, the current regulator being connected to the microprocessor, and a display device with keyboard connected to the microprocessor. This circuit allows fully automatic and rapid and reproducible work and can also be operated by the layman.

DESCRIPTION OF THE DRAWINGS

The invention is now described using a preferred illustrative embodiment. The drawings show.

DETAILED DESCRIPTION

A metal plate 16 is rectangular, heavy and rigid. It stands on two bolts which are screwed into the bottom of the plate 16 and which have hardened faces shaped as hemispheres 17 and 18. The lie symmetrical about a central plane 19 and symmetrical about a tranverse plane 21 which is perpendicular to the central plane 19 and parallel to the front edge 22 of the plate 16. The transverse plane 21 lies close to the front edge 22. Near to a rear edge 23 the plate 16 has a hole 24 in which can be found a transistor 26 which serves as the third but fixed foot. The transistor 26 also serves as a heat sensor with which the temperature of the material 27, the properties of which are to be measured as a function of the penetration behaviour, can be measured. Vertical support columns 28 are screwed into the areas near to the front edge 22 and the rear edge 23. A rigid, heavy metal cover plate 29 is screwed onto these from above. This forms together with the plate 16 and the support columns 28 a very rigid, heavy, protective and, in addition, sufficiently heavy cage. In the central area a rotary magnetic assembly 31 is to be found on the plate 16. This is commercially available. It is fastened rigidly to the plate by means of an end frame 32. in order to set the substantially circular cylindrical rotary magnetic assembly 31 as low as possible, a depression 33 forming a section of a cylinder is provided beneath this in the plate 16 in which the rotary magnetic assembly 31 is partially countersunk. The drive shaft 34 of the rotary magnet assembly 31 passes through the end frame 32, whereby the drive shaft 34 runs parallel to the transverse plane 21. The drive shaft 34 carries a lever 36 with a left arm 37 and a right arm 38. The lever 36 is made of metal, is heavy and, due to its broad shape, is absolutely rigid for the present purposes in the direction of rotation 39. The lever 36 is carried round absolutely proportionally by the drive shaft 34.

The left and right arms 37, 38 are formed by a central piece 41 which runs parallel to the central plane 19 and extends beyond the periphery of the end frame 32 and the rotary magnet assembly 31. At each end is a 90° angle 42, 43 pointing inwards which still as a single block runs into an end piece 44, 46, whereby the end pieces 44, 46 are just as broad as the central piece 41. In the measurement position, the end pieces 44, 46 run parallel to the transverse plane 21 and are, of course, also parallel to each other. A mechanical stop 47 is provided between the central piece 41 and the plate 16. When the central piece 41 contacts the stop 47, the lever 36 has reached its furthest position in the clockwise direction as per FIG. 1. If no counterforces are present, two permanent magnets of opposite poles 48, 49 hold the lever 36 in this position. Furthermore, the right arm 38 with its end piece 46 carries a counterweight 51 which balances with respect to the drive shaft 34 the weight of the left arm 37 including those parts, to be described later, connected to it.

In accordance with FIG. 2 a terminal board 52 to which two wires 53, 54 are led is to be found on top of the end frame 32. The familiar rotary magnet assembly 31 is designed to give a quite exact, reproducible torque to the drive shaft 34 when the current in the wires 53, 54 reach a particular level. The rotary magnet assembly 31 can be driven constantly without damage with the drive shaft 34 held stationary.

The end piece 44 extends significantly beyond the centrakl plane 19 and carries on its front face in FIG. 2 a metal support block 56 which extends on both sides of the central plane 19 and which is rigidly fastened by a means not shown. This has in particular the shape drawn in FIG. 5 to the scale as per FIG. 2. Its base 57 is of cubical shape. A blind threaded hole 59 is bored into its bottom face 58.

Figures 5, 6:
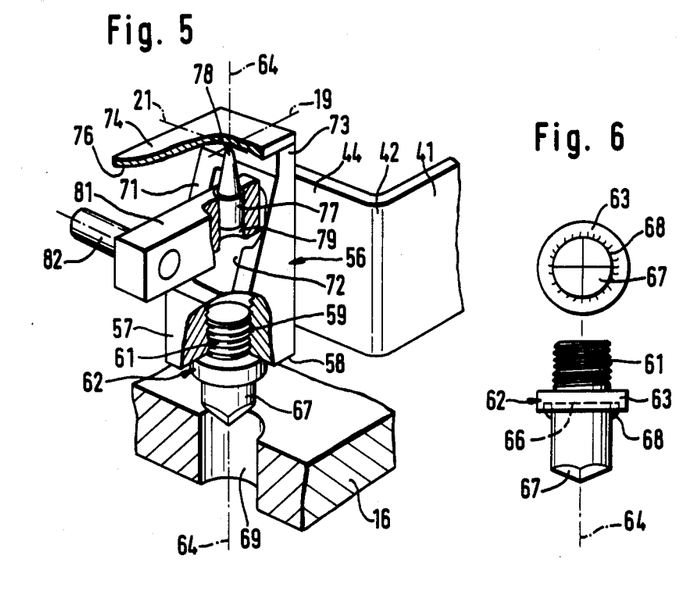
FIG. 5 A detailed view from FIG. 2 to the same scale as FIG. 2.
FIG. 6 The side view and bottom view of a Vickers diamond.

In this a threaded post 61 of a mount 62 is screwed in as far as its circular disk shaped collar 63. The collar 63 is coaxial with its vertical axis 64, which also corresponds to the central axis of the threaded blind hole 59, the threaded post 61, and a recess 66. A Vickers diamond 67 extends with its top front face and the top region of its shaft into the recess 66 and is fixed there with solder 68. It lies coaxial to the axis 64. Its shape is described in DIN 50133. Its lower region has the shape of a pyramid with an angle of flare of 136°. Its tip is flattened for a length of 2 $\mu$m. The axis 64 runs through this tip. A through-hole 69 aligned with the axis 64 in the plate 16 allows the Vickers diamond 67 to pass through the plate 16. If the stop 47 of the right arm 38 is reached, the Vickers diamond 67 is withdrawn from the through-hole 69 and cannot be damaged. Since in the illustrative embodiment a rotary magnetic assembly and not another form of electromotive drive, such as a linear motor or similar, has been used, the Vickers diamond 67 describes a small arc. Thus, the position of the axis 64 also changes slightly during this movement. This is, however, not significant. Only then, when the tip of the Vickers diamond 67 is in contact with the top surface of the material 27, is the axis 64 to be perpendicular to the appropriate surface segment of the material 27.

Figure 7:
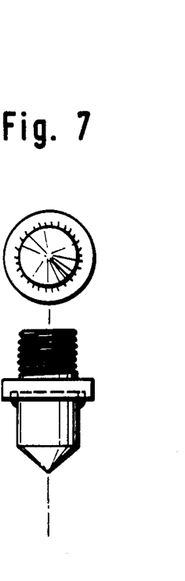
FIG. 7 The side view and bottom view of an optional Rockwell diamond together with mount.
Figure 8:
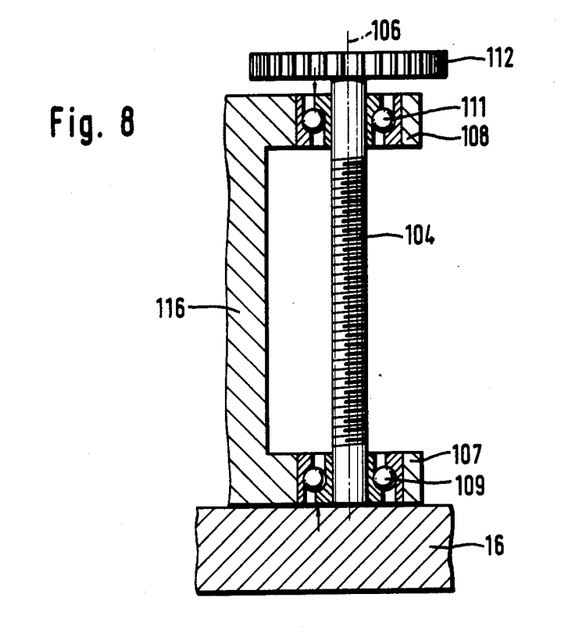
FIG. 8 A section in the area of the threaded screw.
Figure 9:
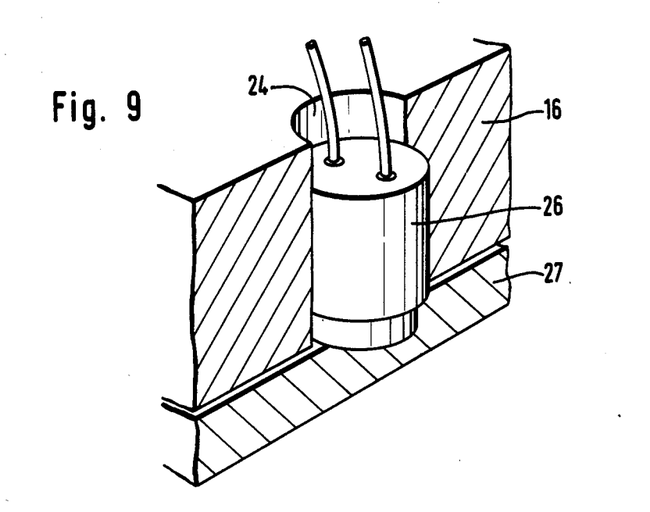
FIG. 9 A perspective view in the area of the third foot of the device.

FIG. 7 shows that a Rockwell diamond can also be used which, in accordance with DIN 50 103, is shaped as a 90° or 120° cone with a rounded tip of radius 0.2 mm.

Depending upon the task on hand, other penetrating body shapes can be used.

Above the base 57 the block forms a wedge 71 which becomes flatter towards the top. Symmetrical to the central plane 19 a groove 72 is provided in the wedge 71 which, in its depth, as per FIG. 5, extends to the right well beyond the axis 64. The top of the wedge 71 extends into a flat bar 73 of the same width. A uniformly thick soft iron plate 74 is to be found on its top face, which runs horizontal. The plate 74 is rectangular and is intersected by the axis 64, the central plane 19 as well as the transverse plane 21. The bottom surface of the plate 74 is provided with a thin gold coating 76. The gold coating has a thickness of 2 $\mu$m.

Below the plate 74 with its direction of action pointing upwards and aligned with the axis 64 is a probe 77 which works on the magnetic distance measurement principle and which has been sold for some years by the applicant under the designation Ga1.3H. The probe 77 has up to now been used for the nondestructive measurement of the thickness of thin coatings which are deposited on a substrate.

The probe type T3.3H of the applicant, which works on the eddy-current principle and which has been available for several years for nondestructive measurement of the thickness of thin coating on nonmagnetic materials, can also be used as the probe 77. In this case, the plate 74 could be made of aluminium and the permanently oxidized surface layer of the aluminium would replace the gold coating.

The spacial configuration is such that the distance between the tip 78 of the probe 77 and the gold coating 76 can be set between zero and a few millimeters in the course of the various still to be described operating status. The thicknes of the gold coating is 2 $\mu$m.

The thickness of the oxide coating on aluminium is common technical knowledge.

As will be explained later, the distance between the tip 78 and the bottom of the plate 74 is the important variable. For this reason, other distance measuring devices of sufficiently fine resolution can be used, such as the capacitive distance measurement method, mirror devices or similar.

The probe 77 is rigidly held in a hole 79 lying coaxial to the axis 64 in the right end of a short, inflexible arm 81 as per FIG. 5 which extends in its right area so far into the groove 72 that the probe 77 can be aligned with the axis 64. Other than shown in FIG. 1, a horizontal shaft 82 at the level of the drive shaft 34 runs parallel to the transverse plane 21 and carries a rigidly fixed arm 81. The shaft 82 is seated at both its ends on pillow blocks 83, 84 which project from the plate 16 rigidly upwards and form a play-free bearing for the shaft 82.

In accordance with FIG. 2a this is achieved in a simple manner, whereby a prismatic groove 86 with flanks symmetrically inclined at 90° to each other is provided in the top faces of the pillow blocks 83, 84. The shaft 82 is seated on the flanks of the groove. Naturally, the grooves 86 are aligned along the geometrical longitudinal axis 87 of the shaft 82. In each case a spring plate 88 is screwed into the top side of each pillow block 83, 84 with a screw 89 and doubly offset in accordance with FIG. 2a. The lobes 91 running above the shaft 82 press said shaft 82 downwards against the flanks of the groove 86 allowing no play. In front of the pillow block 83 a collar 92 is screwed onto the shaft 91 so that this cannot move backwards. A second but larger collar 93 is screwed into the section of the shaft 82 which extends beyond the pillow block 84 which, however, does not contact the pillow block during operation and only prevents the shaft 82 from moving too far forwards as per FIG. 2 during assembly or if knocked.

Figure 3:
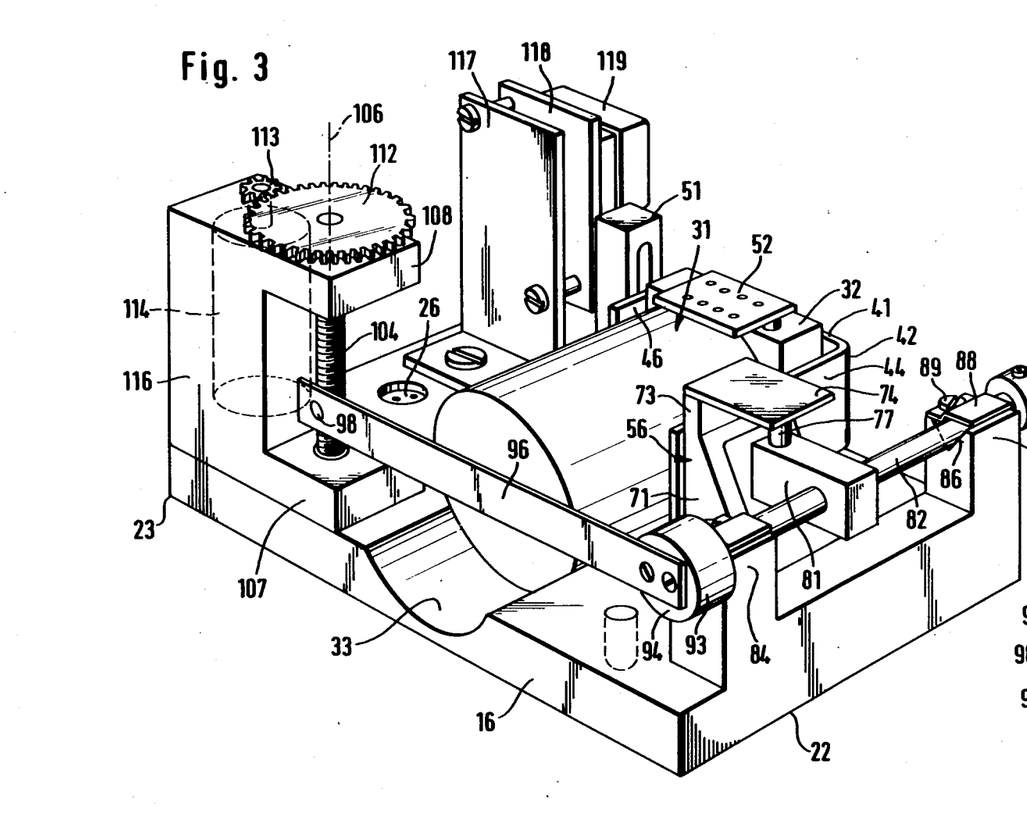
FIG. 3 A prospective rear view of FIG. 2 to the same scale, however, without the cover plate.
Figure 3A:
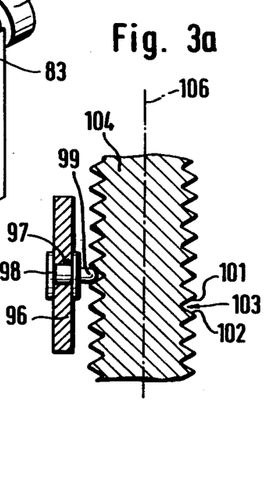
FIG. 3a A cross-section through a sectioned threaded spindle including active connecton to a leaf spring.

The left end of a leaf spring 96, which has a rectangular cross-section, is fastened to the back face of the collar 93 as per FIG. 2. This is much thinner than wide and runs parallel to the central plane 19 in its rigid direction. Accordingly, its flexible direction runs perpendicular hereto, i.e. also perpendicular to the geometrical longitudinal axis 87. As can be seen particularly clearly in FIG. 3, the leaf spring 96 runs behind the rear of the rotary magnet assembly 31 without contacting it. It extends over roughly three quarters of the length of the plate 16 and is, thus, comparatively very long. At its right end as per FIG. 2 is located a through-hole 97 as per FIG. 3a in which a rivet 98 is located. The leaf spring 93 is made of spring steel and somewhat pretensioned so that the right end as per FIG. 2 of the leaf spring 96 is pushed forwards. As per FIG. 3a, the rivet has a brass cup 99 on its right-hand side which extends towards the right in the shape of a hemisphere. In accordance with FIG. 3a, this hemisphere is pressed into the flanks 101, 102 of a thread 103, which is broad enough to allow the cup 99 to partially engage. The spindle 104 carrying the thread is made of brass and is arranged at a distance parallel to the central plane 19. It can be rotated about its geometrical longitudinal axis 106. There must be no backlash in the longitudinal direction. To this end, two bearing plates 107, 108 are provided, which are fastened rigidly to the plate 16 and lie horizontal and separated according to the figures. Each of thse bearing plates 107, 108 carries a collar bearing 109, 111, whereby the collar bearing 111 prevents the spindle 104 from moving downwards and the collar bearing 109 prevents the spindle from moving upwards. The collar bearings 109, 111 are designed as ball bearings. In order to provide sure guidance, the cup 99 presses deep into the thread 103 on the 90° flanks 101 and 102 as per FIG. 3a and, in addition, lies in that plane which stands parallel to the central plane 19 and which runs through the geometrical longitudinal axis 106. The top end of the spindle 104 passes through the bearing plate 108 and the collar bearing 111 and carries rigidly a comparatively large gear wheel 112 which revolves perpendicularly to the central plane 19.

The gear wheel 112 engages a much smaller gear wheel 113. The gear wheel 113 is driven by a reduction gear which is not illustrated and which, for its part, is driven by an electric motor 114 which is to be found in the rear right hand corner as per FIG. 2. The electric motor 114 is located in a housing 116 which is fastened rigidly to the plate 16 and which is connected rigidly and in one piece to the bearing plates 107, 108.

In the area in front of the support column 28 as per FIG. 2 an angle iron 117 is screwed to the plate 16, the vertically standing leg of which carries a board 118, which, in turn, carries a start switch 119.

All the parts described up to now are located in a housing, the bottom of which is the bottom of the plate 16. The start switch 119 projects out of the housing wall. If the device is to be used as a battery operated device, then, no other wires run from the device. Otherwise, the wires required for the rotary magnet assembly 31, the probe 77 and the electric motor 114 are run out.

Figure 10:
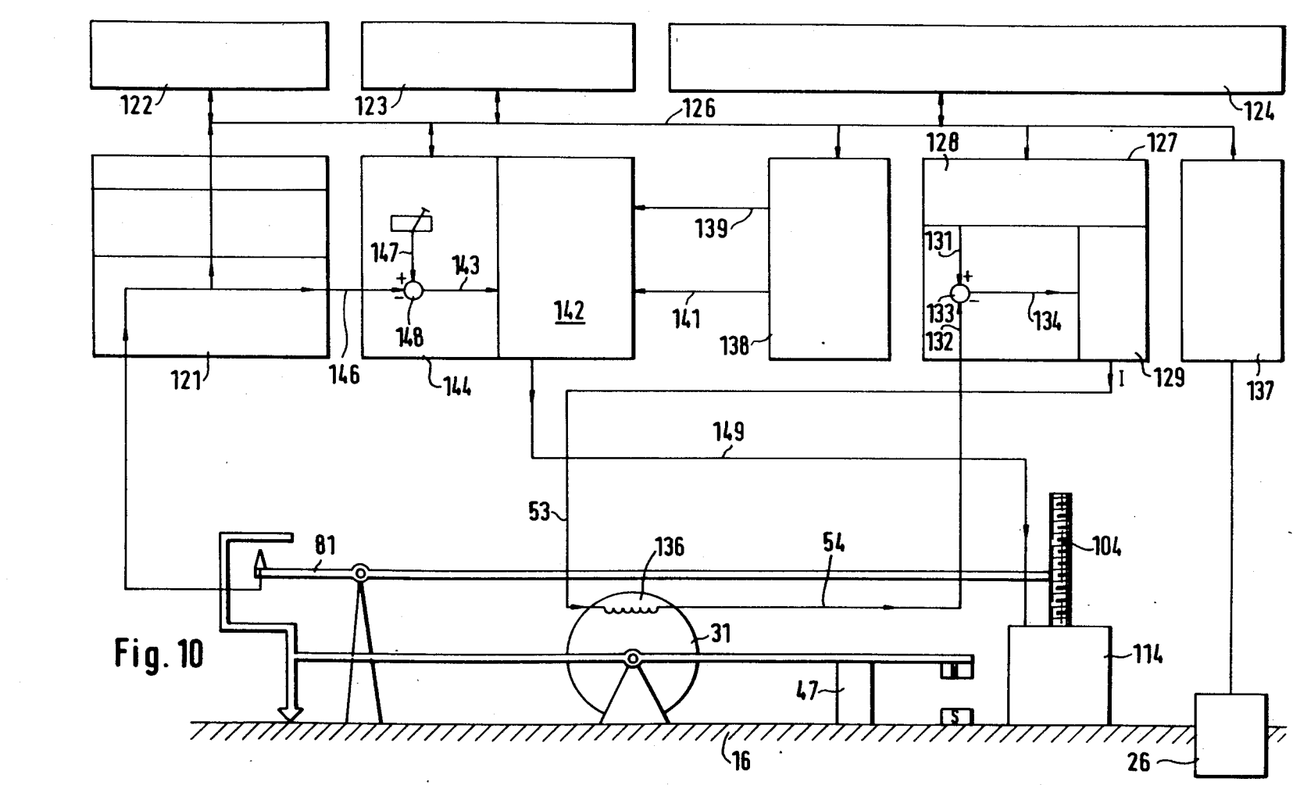
FIG. 10 An electromechanical circuit diagram.

FIG. 10 shows the components already known from the application mentioned at the beginning, namely: the distance measuring circuit 121 which corresponds to the there mentioned coating thickness measurement circuit 94 and which contains and A/D converter.

A coating thickness measurement is nothing more than a distance measurement. In the present invention the evaluation is not made in the form of a coating thickness, rather in the form of a distance which is to be explained later. Moreover, the display and keyboard 122, the interface 123, the microprocessor 124, the bus 126, the rotary magnet circuit 127, the programmable current regulator 128, the rotary magnet final control element 129, the nominal current wire 131, the actual current wire 132, the nominal-actual comparator 133, the wire 134, the wires 53, 54, the coil 136 and the temperature measuring circuit 137 can all be recognized.

A motor contol 138 from which run a motor on-off wire 139 and a motor nominal/infinite wire 141 is new. These wires 139, 141 run to a motor final control element 142. This receives a signal from the nominal-actual comparator line 143 as well which comes from a nominal distance circuit 144. This is fed by a not yet digitalized voltage from the probe 77 via a wire 146 which represents the distance between the tip 78 and the probe 77 on one hand and the plate 74 on the other hand. The nominal distance circuit 144 sends the nominal distance value via a nominal wire 147 to a nominal-actual comparator 148, and the result of the nominal-actual comparison is fed at the correct point in time to the motor final control element 142 via the wire 143. This drives the motor 114 either clockwise or anti-clockwise via a wire 149.

The device works as follows, whereby an initial prerequisite is that it has been calibrated and initialized:

Because of the permanent magnets 48, 49, the right arm 38 contacts the stop 47. The Vickers diamond 67, thus, finds itself in its topmost position and has been safely raised from the material 27. The tip 78 contacts the gold coating 76 which corresponds to the distance 0. A current is supplied to the coil 136 via the wires 53, 54 which sets a counter-torque to the permanent magnets 48, 49. A nominal distance of 40 μm is programmed into the nominal distance circuit either permanently or by the microprocessor 124. This nominal distance is to be maintained by the probe 77. The motor final control element 142 drives the motor such that the probe 77 moves downwards. Since the coil 136 is still generating the counter-torque, the point 78 remains in contact with the gold coating 76 during the regulating procedure. Thus, the left arm 37 turns counter-clockwise as does the arm 81 in the general arrangement diagram of FIG. 10. In the actual embodiment, the arm 81 turns clockwise because it has the same direction as the leaf spring 96. This regulating procedure allows the probe 77 and the plate 74 to move downwards. At a particular point in time, the tip of the Vickers diamond 67 touches the surface of the material 27 and does not move any further since the torque generated by the coil 136 is just sufficient to counteract the force of the permanent magnets 48, 49 but not sufficient to press the tip of the Vickers diamond 67 into the material. The Vickers diamond has set down fully bounce-free because the tip 78 continually supports the plate 74, and because of the obvious lever reductions, the spindle 104 and the high reduction from the motor 114 at the threaded screw 104, the probe sinks very slowly. The torque of the rotary magnet assembly 31 is, thus, maintained at a low level. Since the nominal distance circuit 144 requires a distance of 40 μm, the motor final control element 142 allows the motor 114 to run until the tip 78 of the probe 77 reaches a distance of 40 μm. At this point the motor 114 is stopped as well.

Figure 11:
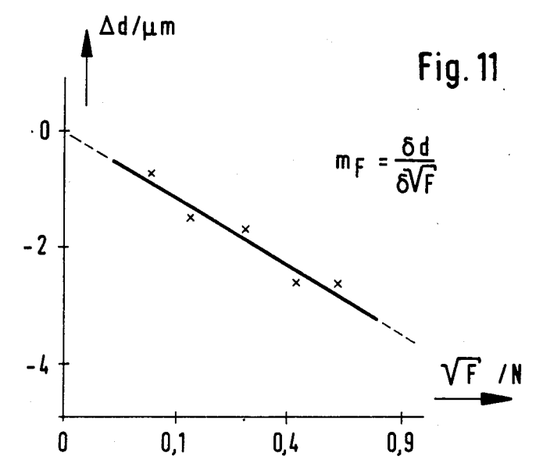
FIG. 11 A diagram in connection with the hardness measurement.
Figure 13:
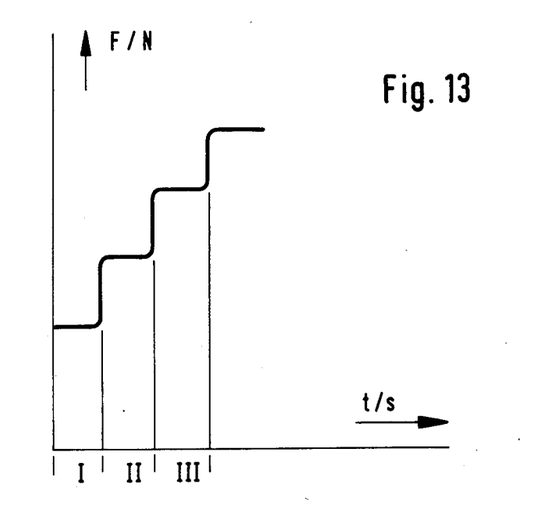
FIG. 13 A diagram showing the force to be applied as a function of time.

As is the case for the application already mentioned at the start, the force F is increased stepwise in accordance with FIG. 13 over the time interval t, whereby the rotary magnet circuit 127 outputs stepwise increasing currents via the wires 53, 54. The time intervals Nos. I, II and III are equal and are typically 0.8 seconds long. The force, thus, increases with time as is shown in FIG. 13. The tip 67 penetrates by a constant amount into the material 27. This amount can be roughly 2% plus 0.1 μm. The force is now increased while, at the same time, the distance associated with each force level is measured between the tip 78 and the plate 74. During measurements, the distance becomes ever smaller. If the distance is 39.5 μm, this means that, after the difference has been taken, the tip of the Vickers diamond 67 has penetrated 0.5 μm into the material 27. This difference is indicated at the display and keyboard 122, is appropriate sent via the interface 123 and fed to the microprocessor system 124. If the force F is increased in accordance with FIG. 13, then, the penetration depth associated with each force level is obtained from the ever decreasing distances. The change in distance Δd is a non-linear function of the force F. If, as per FIG. 11, Δd is plotted against √F, it can be seen that a linear relationship results. The slope $m_F$, calculated according to FIG. 11, is an unambiguous measure of the hardness at the surface of the material 27. Thus, the following can be defined:

$$\text{Fischer-hardness} = \frac{1}{m_F} = \frac{\delta \sqrt{F}}{\delta d}$$

Figure 14:
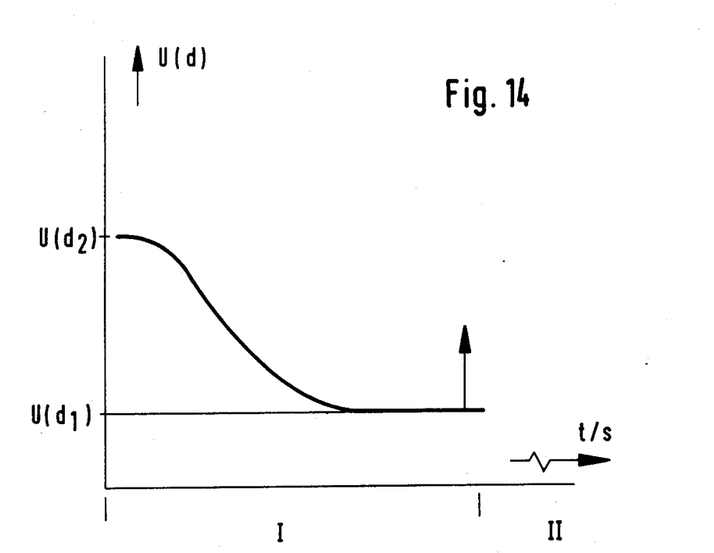
FIG. 14 The voltage output by the probe as a function of one of the time intervals as per FIG. 13.

FIG. 14 shows the voltage U (d) output by the probe 77 as a function of time during the time interval No. I from FIG. 13. Since the voltage U (d) output is a non-linear function of the difference in distance (d), the change in distance difference from the difference of the two values U (d1)-U (d2) is so transformed in the distance measuring circuit 121 that the measured value is directly proportional to the measured variable. The voltage U (d) cannot spontaneously follow the force F due to the resistance moment resulting from the penetration of the Vickers diamond 67 into the surface of the material 27. For this reason, the increment of current I, which flows through the wires 53, 54, is selected such that the voltage U (d) remains almost constant when the voltage value is read. This point in time is shown in the right for FIG. 14 by an arrow which points upwards. It can be seen that the voltage is read immediately before the period II starts. The same is true of the second and third periods, the measured values are initially stored and processed further so that the transformed linear relationship as per FIG. 11 results.

Figure 12:
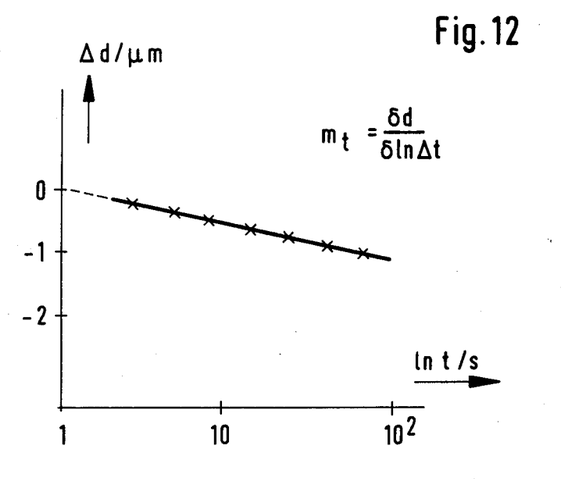
FIG. 12 A diagram in connection with the flow behaviour.

If the material is soft, it is possible that the maximum allowable penetration depth of 40 μm is not sufficient. In this case, the nominal distance circuit 144 is supplied with a nominal distance of, for example, 100 μm or more. If, instead of the hardness, the flow behaviour of material 27 is to be determined, then, the change in distance difference δd is read in logarithmic equidistant time intervals as per FIG. 12. This information is processed and displayed at the display and keyboard 122. The slope of the straight line shown in FIG. 12 is a direct measure of the flow behaviour. The slope equation is given in FIG. 12.

The microprocessor 124 drives the rotary magnet assembly 31 with a contant current which is appropriate to the torque output. Since the microprocessor 124 knows the distance of the tip of the Vickers diamond 67 from the geometrical longitudinal axis of the drive shaft 34, it can calculate from these variables the force F. Due to the constant current, temperature fluctuations have no effect on the coil resistance of the rotary magnet assembly 31, since the increment of force F is, in any case, constant.

The interface 123 can serve various purposes. For example, a printer can be connected up to it which outputs such characteristic curves as can be seen in FIG. 11 and FIG. 12.

Figure 1:
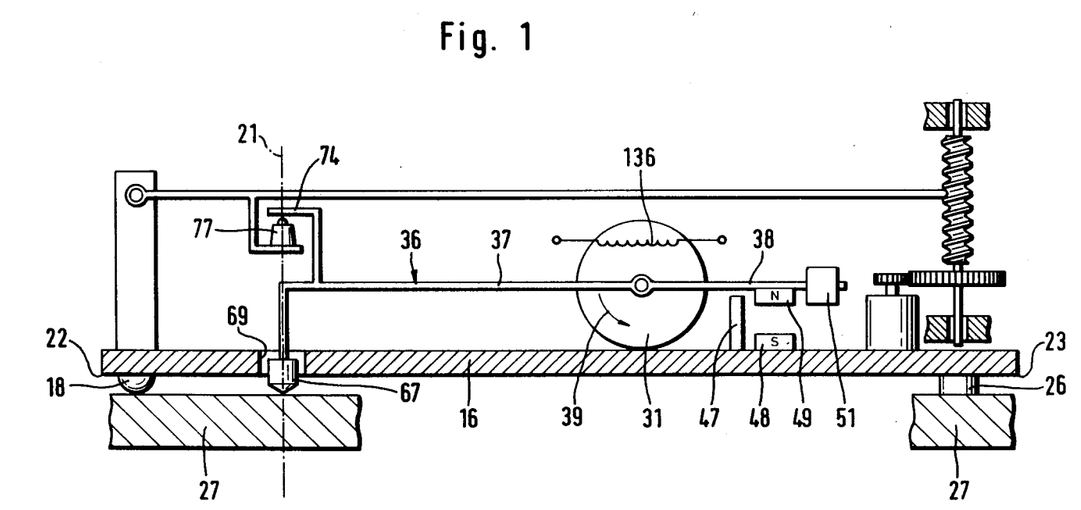
FIG. 1 A side view showing the general arrangement.

The tip of the Vickers diamond 67 moves along an arc. The design is such that in a particular position it stands fully perpendicular to the flat surface of the material 27. If the surface of the material 27 lies above or below this ideal position, then, of course, the Vickers diamond 67 is no longer exactly perpendicular. However, in practice, this is of no significance: If it is assumed that the left arm 37 as per FIG. 1 is 35 mm long and the top surface of the material 27 lies ±1 mm away from its ideal position, then, this results in an error of 0.04% which is far below any measurement uncertainty. For clarity, the above procedure is explained once more by the following flow diagram:

As can be seen from the flowchart above and as has already been mentioned, the system must be initially calibrated. The procedure is the following: After switch-on, it can be seen that the tip 78 is at a specific distance from the plate 74 which, for example, is roughly of the order of 40 μm. The motor 114 is now switched on. The plate 74 stays in its position because of the stop 47 and the permanent magnets 48, 49. The probe 77 is moved away from the plate 74 until the change in voltage dU/dt=zero. This means that the probe 77 is now so far removed from the plate 74 that it is no longer damped. This distance can, thus, be assumed to be "infinity". Thisvoltage is taken by the microprocessor 107 and stored. Thereafter, the probe 77 is driven to the nominal distance of, for example, 40 μm so that the system knows the two values "infinity" and "nominal distance". In the field of thickness measurement, calibration is accomplished when one knows two values and the characteristic curve of "law" according to which a magnetic probe such as probe 77, function. In this case the values are infinity and the nominal distance of 40 μm. The system is now ready for measurement which was the prerequisite at the start. The steps required for initialization are explained once again using the following flow diagram:

Because the arm 81 extends in the same direction as the leaf spring 96 and, thus, one lever of the double lever points in the direction of the rotary magnet assembly 31, at least one length of construction is saved on one hand, and on the other the lever 37 can be made short enough, the lever arrangement is more simple and the alignment with the Vickers diamond 67 is more easily attained. If the constructional length is not important, a lever configuration as per FIG. 1 can also be selected.

The measuring range of the apparatus according to the nvention is extraordinarily wide. The hardness of very thin quartz coatings as sued for antireflexion properties in spectacle lenses can easily be measured. At the same time, very soft rubbery elastic materials can be measured.

Figure 4:
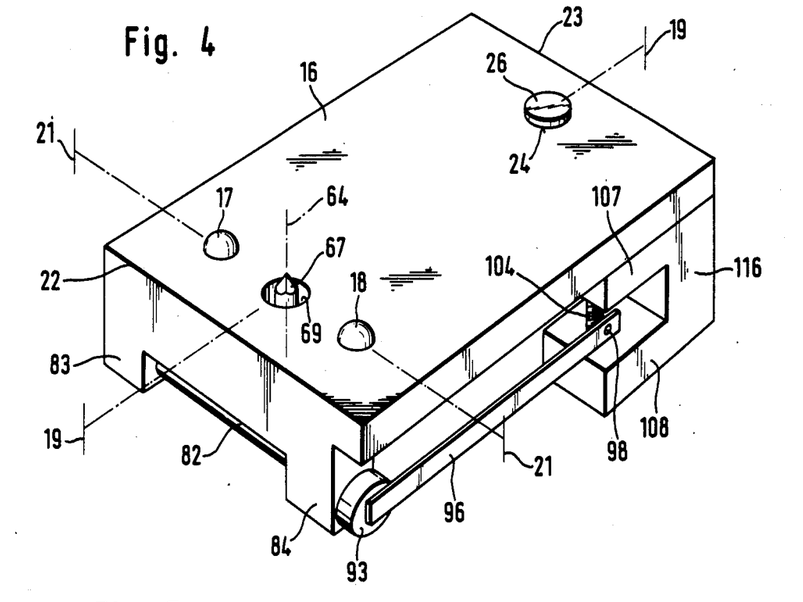
FIG. 4 The bottom view of FIG. 3.

It is even possible to check whether the surface of the material to be measured is clean: If, for example, the abovementioned quartz coating is not washed with methylated spirit prior to measurements, then, the "hardness" of any layer of dirt is measured. This fact is easily recognized since the measurement points are scattered much too much about the straight line shown in FIG. 4.

If the material to be measured has a perfectly good surface and the measurement points are scattered more than the regression law allows, then, it can be seen that these are unusable in correct measurements, whereby the error may stem from various sources. The measurement points, must, in fact, lie as near to the straight line or on the straight line as may be required by the law of regression. Incorrect measurements can, therefore, be very easily sorted out.

The device is working in the elastic range (Hook). No permanent deformations are left.

I claim:

1. In an apparatus for nondestructive, absolute measurement of the properties of solid materials which is derived from the behavior of a body penetrating said materials, having a penetrating body, a guidance device for guiding said penetrating body in a direction of motion onto said materials, and an electrical evaluation circuit, the improvement comprising:

(a) an electromotive drive connected to said guidance device that urges said penetrating body with a specific, but variable force onto the surface of said materials, (b) means for feeding a first voltage output representing said force to said electrical evaluation circuit, (c) a floating distance-measuring device having first and second sections which allows measurements of the distance between said first and second sections in said direction of motion of said penetrating body and has a resolution that is significantly smaller than the depth of penetration of said penetrating body, (d) said first section being rigidly connected to said penetrating body, (e) a follower connected to said second section to guide said penetrating body, through said first section, bounce-free onto the surface of said material, (f) means for finely moving said follower in said direction of motion of said penetrating body, said means switching off after said penetrating body has been set down onto said material and when said distance-measuring device measures a prespecified distance between said first and second sections, and (g) means for feeding a second voltage output representing the depth of penetration from said distance measuring device to said electrical evaluation circuit.

2. The improvement as claimed in claim 1, wherein said electromagnetic drive has a drive shaft and said guidance device is a lever rigidly fixed to said drive shaft which carries said penetrating body tangential to the rotary motion of said drive shaft.

3. The improvement as claimed in claim 1, wherein said penetrating body is a diamond.

4. The improvement as claimed in claim 3, wherein said diamond is a pyramid-shaped Vickers diamond.

5. The improvement as claimed in claim 3, wherein said diamond is a conical Rockwell diamond.

6. The improvement as claimed in claim 1, wherein said penetrating body is a Brinell steel ball.

7. The improvement as claimed in claim 1, wherein said penetrating body is exchangeable and screwed into said guidance device.

8. The improvement as claimed in claim 1, including means for exerting a permanent force gently on said guidance device for biasing said guidance device against said direction of motion of said penetrating body.

9. The improvement as claimed in claim 8, wherein said permanent force means comprises at least one magnet.

10. The improvement as claimed in claim 9, including two magnets aligned in the direction of motion of said penetrating body.

11. The improvement as claimed in claim 8, including a stop for said guidance device which limits the movement of said guidance device with respect to the direction of motion of said penetrating body.

12. The improvement as claimed in claim 1, wherein said distance-measuring device comprises a probe for measuring thin coatings fixed to one of said two sections and a facing layer fixed to the other section.

13. The improvement as claimed in claim 12, wherein said probe works on the eddy-current principle.

14. The improvement as claimed in claim 12, wherein said distance-measuring device has a resolution that lies in the range of at least one hundredth of a micrometer.

15. The improvement as claimed in claim 12, wherein said probe works on the magnetic field principle.

16. The improvement as claimed in claim 12, wherein said probe is a capacitive probe.

17. The improvement as claimed in claim 12, wherein said probe works on the field-plate principle.

18. The improvement as claimed in claim 12, wherein said counter-pole body comprises a metallic substrate having an inert thin coating.

19. The improvement as claimed in claim 18, wherein said inert thin coating is a gold coating.

20. The improvement as claimed in claim 12, wherein said facing layer is arranged perpendicular to the longitudinal axis of said probe.

21. The improvement as claimed in claim 12, wherein said counter-pole body is quasi infinitely large with respect to the probe field.

22. The improvement as claimed in claim 12, wherein said probe is secured on said follower and said facing layer is secured on said guidance device.

23. The improvement as claimed in claim 1, wherein said distance-measuring device is aligned with said penetrating body, as seen from the direction of motion of said penetrating body.

24. The improvement as claimed in claim 1, wherein said follower includes a threaded spindle.

25. The improvement as claimed in claim 24, wherein said threaded spindle stands parallel to the direction of motion of said penetrating body.

26. The improvement as claimed in claim 24, including an electric motor that drives said threaded spindle, and means for effecting substantial gear reduction between said electric motor and said threaded spindle.

27. The improvement as claimed in claim 26, wherein said electric motor is at the other side of said electromotive drive, as seen from said probe, and comprising a device base to which said electric motor is fastened at one end.

28. The improvement as claimed in claim 24, wherein said threaded spindle has bearings at both ends, and at least one of said bearings is a collar-bearing.

29. The improvement as claimed in claim 1, including a pivoting shaft close to said distance-measuring device and perpendicular to the direction of motion of said penetrating body, wherein one of said two sections of said distance-measuring device is fastened to said pivoting shaft.

30. The improvement as claimed in claim 29, wherein a single, two-ended lever is fastened at one end to said pivoting shaft, and a threaded spindle guides said two ended lever at its other end.

31. The improvement as claimed in claim 30, wherein said lever is a broad leaf spring, the rigid direction of which lies parallel to its direction of movement, having a cup at its other end which engages without play on the flanks of the thread of said threaded spindle, and is pressed into said thread in the bending direction for pretensioning said leaf spring.

32. The improvement as claimed in claim 31, wherein the pretensioning is so light that, when said leaf spring arrives at its end position, the cup disengages the thread.

33. The improvement as claimed in claim 29, wherein said electromagnetic drive has a drive shaft and said pivoting shaft and said drive shaft are arranged parallel to each other and at the same level.

34. The improvement as claimed in claim 1, including a device base that stands on three feet, two of which lie on a common line with the tip of said penetrating body.

35. The improvement as claimed in claim 34, wherein said common line runs parallel to one of the lateral edges of the device.

36. The improvement as claimed in claim 34, wherein said two feet living on said common line have hardened faces shaped as hemispheres.

37. The improvement as claimed in claim 1, including a start switch.

38. Method for calibrating an apparatus for non-destructive, absolute measurement of the properties of solid materials which is derived from the behavior of a body pressing onto said materials, said apparatus having a guidance device for guiding said penetrating body in a direction of motion onto said materials, an electromotive device connected to said guidance device that urges said penetrating body with a specific, but variable force onto the surface of said material, a floating distance-measuring device having first and second sections, which allows measurements of the distance between said first and second sections in the direction of motion of said penetrating body, and has a resolution that this significantly smaller than the depth of penetration of said penetrating body, said first section being connected to said penetrating body and said second section being connected to a follower to guide said penetrating body through said first section, bounce-free onto the surface of said material, means for finely moving said follower said direction of motion of said penetrating body, said means switching off after said penetrating body has been set down onto said material and when said distance-measuring device measures a nominal, prespecified distance between said first voltage output representing said force and a second voltage output representing the depth of penetration from said distance measuring device to an electric evaluation circuit, said method comprising:
  (a) switching on the apparatus,
  (b) bringing said distance-measuring device to a position that corresponds to a first distance value,
  (c) storing said first distance value in a memory device, and
  (d) entering said nominal prespecified distance as a second value into said memory device.

39. Method as claimed in claim 38, wherein said first value corresponds to a value which is nearly the same as the value of a layer of infinite thickness.

40. Method as claimed in claim 38, wherein said second value corresponds to a value which is very much larger than that of the anticipated penetration depth.

41. Method as claimed in claim 40, wherein said nominal distance value lies in the deca micrometer range.

42. Method as claimed in claim 41, wherein said nominal prespecified distance value is 40 $\mu m +/- 30\%$.

43. Method as claimed in claim 40, wherein said nominal prespecified distance value is between 10 and 80 $\mu m$.

44. Circuit for evaluating signals received from an apparatus for non-destructive, absolute measurement of the properties of solid materials which is derived from the behavior of a body pressing on said materials, said apparatus having a guidance device for guiding said penetrating body in a direction of motion onto said materials, an electromotive device connected to said guidance device that urges said penetrating body with a spcific, but variable force onto the surface of said material, a floating distance measuring-device having first and second sections, which allows measurements of the distance between said first and second sections in the direction of motion of said penetrating body and has a resolution that is significantly smaller than the depth of penetration of said penetrating body, said first section being rigidly connected to said penetrating body and said second section being connected to a follower to guide said penetrating body through said first action, bounce-free onto the surface of said material, means for finely moving said follower in the direction of motion of said penetrating body, said means switching off after said penetrating body has been set down onto said material and when said distance-measuring device measures a specified distance, and means for feeding a first voltage output representing said force to said signal evaluating circuit and a second voltage output representing the depth of penetration from said distance-measuring device to said signal evaluating circuit, said circuit comprising an A/c converter connected to said distance measuring device, a distance nominal-actual comparator driven by said A/D converter at its actual input, a motor final control element driven by the nominal-actual output of said comparator, a follower servomotor driven by said motor final control element, a motor control for driving said motor final control element via a "motor on/off line" and a "motor nominal value/infinity line", a microprocessor connected to said motor control, a programmable current regulator having a current nominal-actual comparator, said electromotive drive being controlled by said current nominal-actual comparator via a current final control element, said current regulator being connected to said microprocessor, and a display device with keyboard connected to said microprocessor.

45. Method for deriving the nondestructive absolute measurement of the properties or solid materials from the behavior of a body pressing onto said materials, in an apparatus having a guidance device for guiding said penetrating body in a direction of motion onto said materials, an electromotive device connected to said guidance device that urges said penetrating body with a specific, but variable force onto the surface of said material, a floating distance-measuring device having first and second sections, which allows measurements of the distance between said first and second sections in the direction of motion of said penetrating body and has a resolution that his significantly smaller than the depth of penetration of said penetrating body, said first section being connected to said penetrating body and said second section being connected to a follower to guide said penetrating body, through said first section, bounce-free onto the surface of said material, means for finely mound said follower in said direction of motion of said penetrating body, said means switching off after said penetrating body has been set down onto said material and when said distance-measuring device measures a prespecified distance, and means for feeding a first voltage output representing said force, and a second voltage output representing the depth of penetration from sad distance-measuring device to an electric evaluation circuit, comprising:
 (a) applying said force on a plurality of equal time intervals in accordance with a square root law to derive a linear relationship between said penetration depth and the square root of said force, and
 (b) relating said penetration depth to said square root of said force to give the degree of hardness as a constant.

* * * * *